(12) United States Patent (10) Patent No.: US 9,044,136 B2
Luo (45) Date of Patent: Jun. 2, 2015

(54) WEARABLE MINI-SIZE INTELLIGENT HEALTHCARE SYSTEM

(75) Inventor: Hongyue Luo, Waterloo (CA)

(73) Assignee: CIM TECHNOLOGY INC., Waterloo, Ontario (CA)

( * ) Notice: Subject to any disclaimer, the term of this patent is extended or adjusted under 35 U.S.C. 154(b) by 872 days.

(21) Appl. No.: 11/675,684

(22) Filed: Feb. 16, 2007

(65) Prior Publication Data

US 2008/0200774 A1    Aug. 21, 2008

(51) Int. Cl.
*A61B 5/00* (2006.01)
*G06F 19/00* (2011.01)
*A61B 5/0205* (2006.01)

(52) U.S. Cl.
CPC ............. *A61B 5/0002* (2013.01); *A61B 5/0024* (2013.01); *A61B 5/02055* (2013.01); *A61B 5/6815* (2013.01); *A61B 5/6838* (2013.01); *G06F 19/3418* (2013.01); *G06F 19/345* (2013.01)

(58) Field of Classification Search
USPC .................. 600/300–301; 178/903–904, 920; 340/539, 573.1–576
See application file for complete search history.

(56) References Cited

U.S. PATENT DOCUMENTS

| 4,679,144 | A |   | 7/1987  | Cox et al. |         |
|-----------|---|---|---------|------------|---------|
| 5,673,692 | A | * | 10/1997 | Schulze et al. | 600/301 |
| 5,694,940 | A |   | 12/1997 | Unger et al. |        |
| 5,971,931 | A | * | 10/1999 | Raff | 600/485 |
| 6,126,595 | A | * | 10/2000 | Amano et al. | 600/300 |
| 6,302,844 | B1| * | 10/2001 | Walker et al. | 600/300 |
| 6,416,471 | B1|   | 7/2002  | Kumar et al. |        |
| 6,443,890 | B1| * | 9/2002  | Schulze et al. | 600/300 |

(Continued)

FOREIGN PATENT DOCUMENTS

CA    2133424    10/1993
CA    2574759    1/2006

(Continued)

OTHER PUBLICATIONS

Nuria Oliver et al., "HealthGear: A Real-time Wearable System for Monitoring and Analyzing Physiological Signals", Tech Report: MSR-TR-2005-182, www.research.microsoft.com.

(Continued)

*Primary Examiner* — William Thomson
*Assistant Examiner* — Bobby Soriano
(74) *Attorney, Agent, or Firm* — Gowling Lafleur Henderson LLP; Neil Henderson

(57) ABSTRACT

A system and method for the wearable mini-size intelligent healthcare system, comprising one or multiple vital signal sensors, activity sensors, a real-time detection and analyzing module for continuous health monitoring, adjustable user setting mode with the adaptive optimization, data-collecting capability to record important health information, smart audio outputs of audio beep and speech advice to the user through audio path and audio interface, preset and user confirmable alarm conditions via wireless communications network to the appropriate individual for prompt and necessary assistance. The system uses noninvasive monitoring technology for continuous, painless and bloodless health state monitoring. The system also works through the short range RF link with carry-on PDA or cell phone for displaying health information, making urgent contact to support center, doctor or individual, or for information transmission with a healthcare center.

18 Claims, 4 Drawing Sheets

Note:
S1: Physiological sensors
S2: Activity sensors
SN: New sensors
RF: Wireless link System Overview

(56) References Cited

U.S. PATENT DOCUMENTS

| | | | |
|---|---|---|---|
| 6,478,736 B1* | 11/2002 | Mault | 600/300 |
| 6,569,094 B2* | 5/2003 | Suzuki et al. | 600/300 |
| 6,579,231 B1 | 6/2003 | Phipps et al. | |
| 6,605,038 B1* | 8/2003 | Teller et al. | 600/300 |
| 6,623,427 B2* | 9/2003 | Mandigo | 600/300 |
| 7,254,516 B2* | 8/2007 | Case et al. | 702/182 |
| 7,652,569 B2* | 1/2010 | Kiff et al. | 340/539.11 |
| 7,657,444 B2* | 2/2010 | Yu | 705/3 |
| 2001/0044588 A1* | 11/2001 | Mault | 600/549 |
| 2004/0077934 A1* | 4/2004 | Massad | 600/300 |
| 2004/0172290 A1 | 9/2004 | Leven | |
| 2005/0033377 A1* | 2/2005 | Milojevic et al. | 607/45 |
| 2005/0093709 A1* | 5/2005 | Franco et al. | 340/686.1 |
| 2005/0148890 A1 | 7/2005 | Hastings | |
| 2005/0245839 A1* | 11/2005 | Stivoric et al. | 600/549 |
| 2006/0064037 A1* | 3/2006 | Shalon et al. | 600/586 |
| 2006/0252999 A1* | 11/2006 | Devaul et al. | 600/300 |
| 2007/0042713 A1 | 2/2007 | Ayed | |
| 2007/0106172 A1* | 5/2007 | Abreu | 600/549 |
| 2008/0146890 A1* | 6/2008 | LeBoeuf et al. | 600/300 |
| 2008/0154098 A1* | 6/2008 | Morris et al. | 600/300 |

FOREIGN PATENT DOCUMENTS

| | | |
|---|---|---|
| CA | 2602899 | 9/2006 |
| CN | 1908668 | 2/2007 |
| GB | 2284060 | 5/1995 |
| GB | 2388194 | 11/2003 |
| WO | WO 01/82789 | 11/2001 |
| WO | WO 2005/039406 | 5/2005 |
| WO | WO 2005/084533 | 9/2005 |
| WO | WO 2006/090371 | 8/2006 |

OTHER PUBLICATIONS

International Searching Authority, International Search Report, Apr. 23, 2008, PCT/CA2008/000195.

International Searching Authority, The Written Opinion of the International Searching Authority, Apr. 23, 2008, PCT/CA2008/000195.

\* cited by examiner

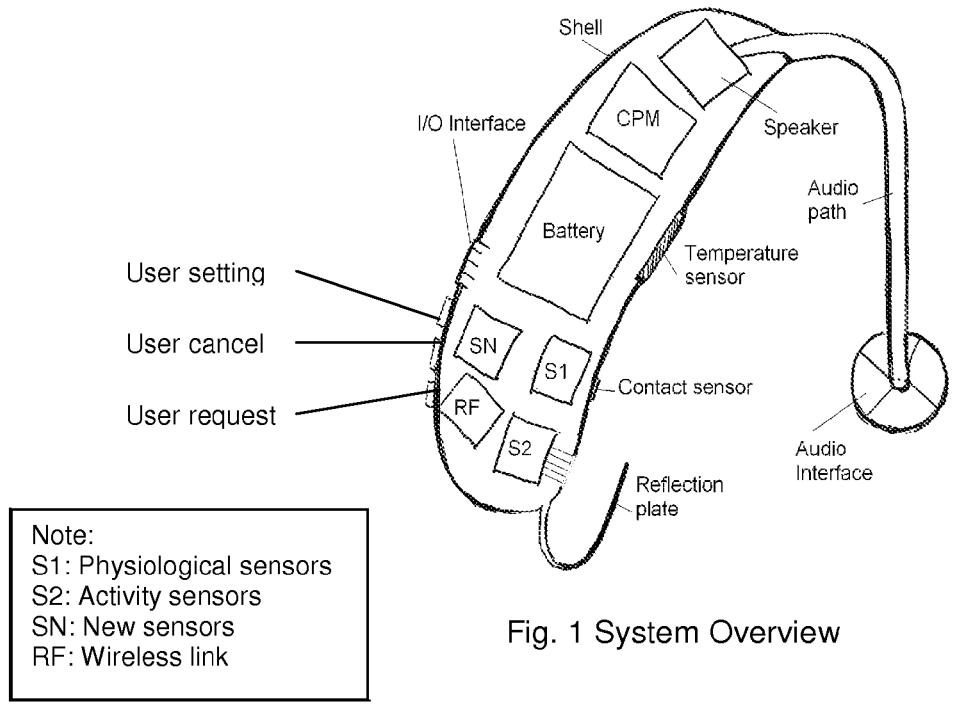
Fig. 1 System Overview
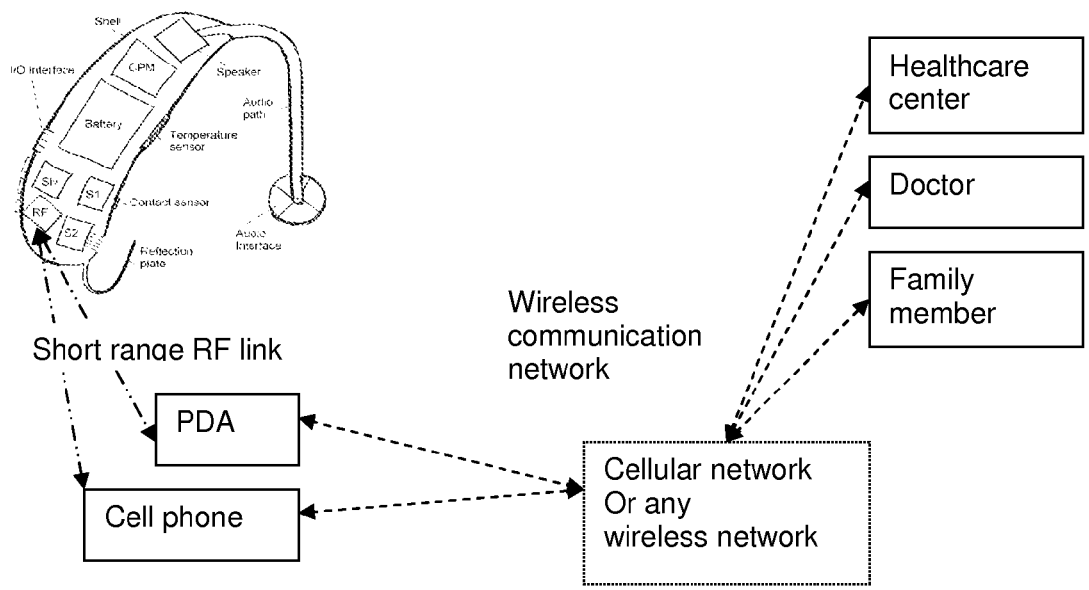
Fig. 2 System application overview

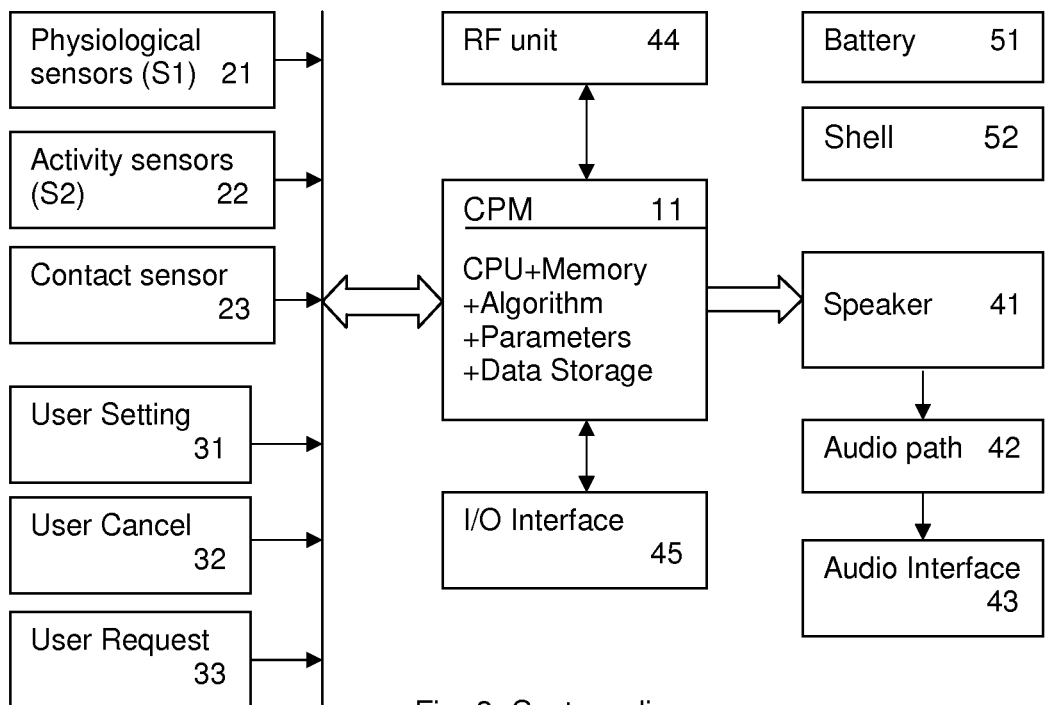
Fig. 3: System diagram
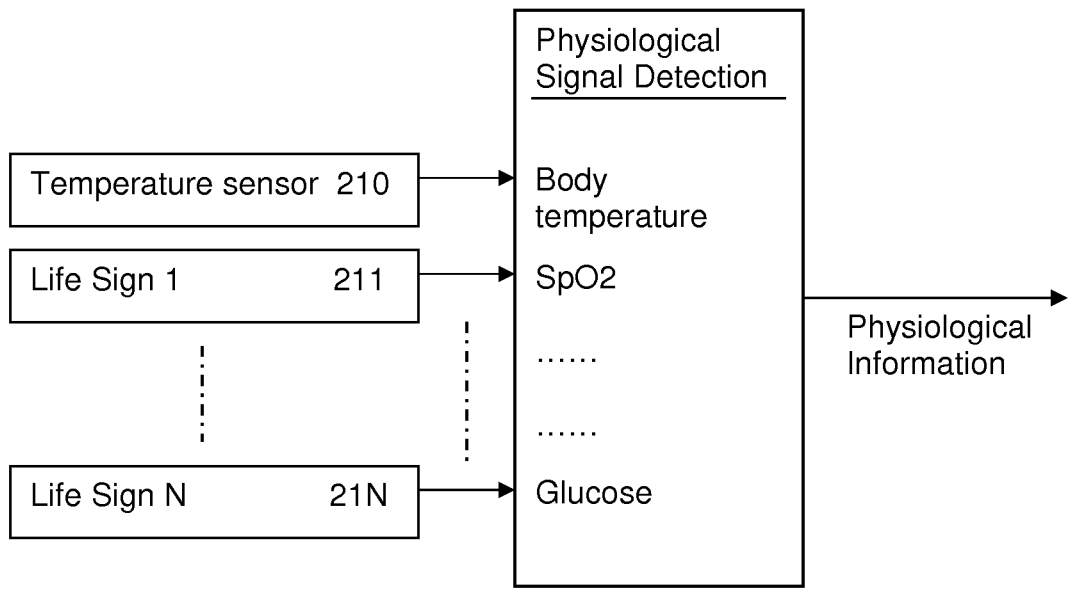
Fig. 4: Physiological Signal Monitoring

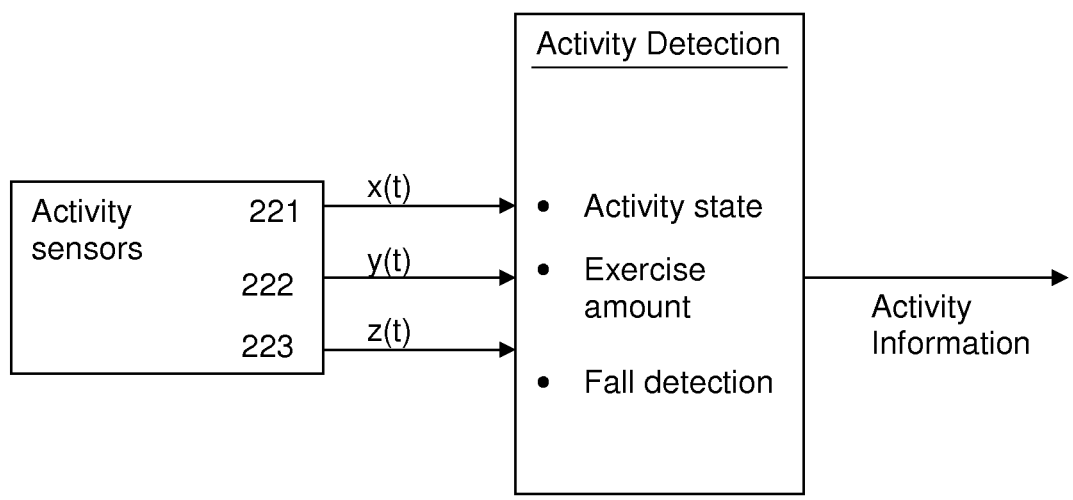
Fig. 5: Activity Monitoring

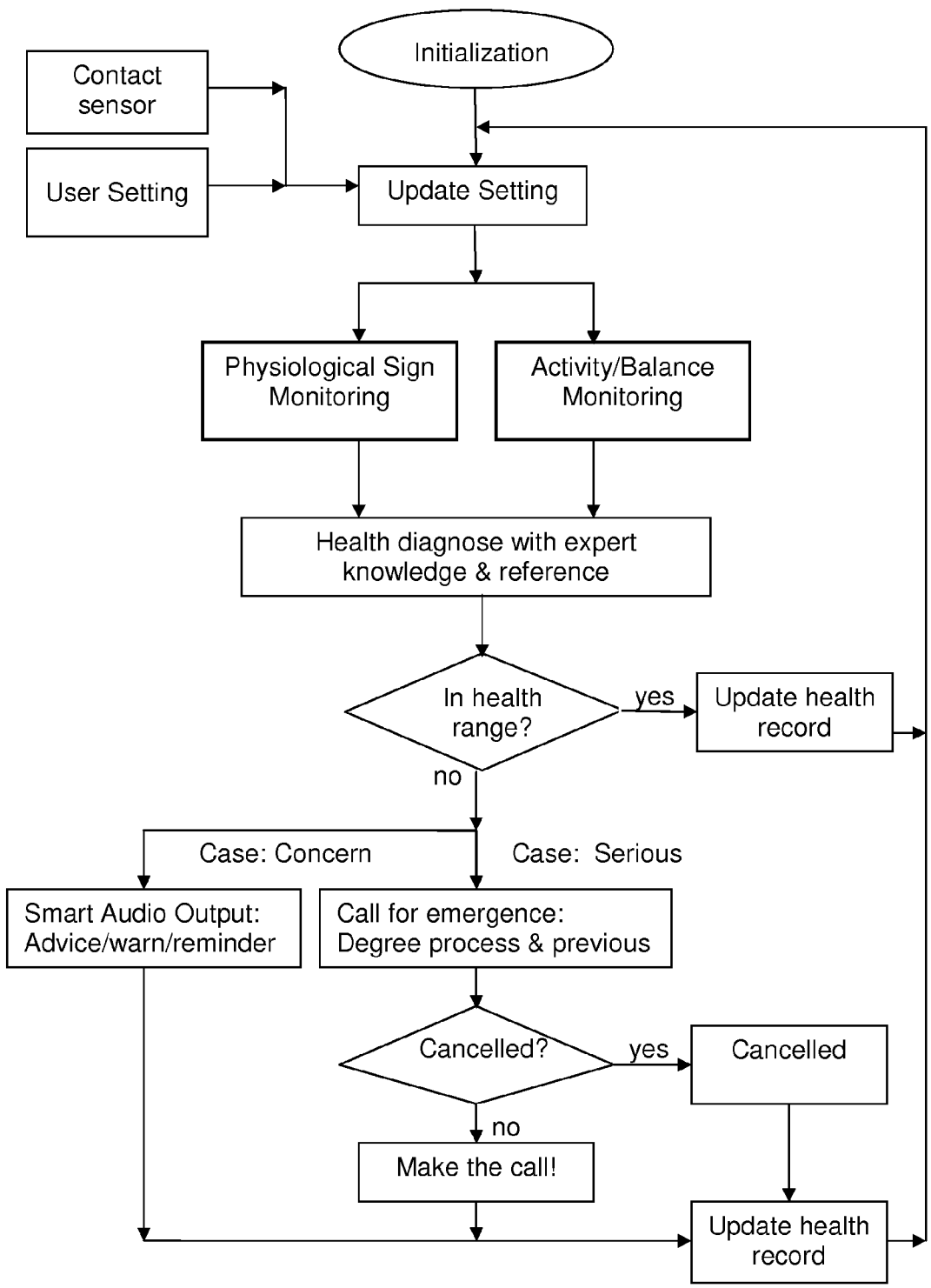
Fig. 6: System Principle

WEARABLE MINI-SIZE INTELLIGENT HEALTHCARE SYSTEM

FIELD OF THE INVENTION

The present invention relates to a wearable mini-size intelligent healthcare system for the continuous monitoring and care of a subject. More particularly, the present invention is for a healthcare system and method, taking advantage of the specific body position around the subject's ear for the continuous detection and analyzing of a subject's health condition with noninvasive monitoring technology, the evaluation of said health condition enabling the early detection of adverse health conditions, the providing of the smart audio interface for real-time notification with emotional perception, health information display or storage over the Personal Digital Assistants (PDA) or cell phone via short range RF link, urgent contact or information transmission through PDA or cell phone over wireless communication network.

BACKGROUND OF THE INVENTION

As well-known, a person with a health issue such as heart disease usually needs to be examined regularly and better to be monitored continually for the early signs of those health problems. Although there are many instruments or devices available for monitoring an individual's activities and evaluating their health states, a person with health issue needs to visit periodically a medical facility to obtain the proper diagnosis and medical treatment. Once at the medical facility, the subject is usually examined with some type of medical instruments for the short duration. The health information obtained during the visit only represents a small portion of the subject's physiological information at the time of the examination, which usually does not reflect the actual health problem occurring in the daily life. In order to obtain more complete medical information, doctors would need to observe a subject's health condition over certain duration usually longer than that of regular health examination. Because of time and costs associated with these tests and observations, it is usually impractical to conduct the required long-term observation and full evaluation for most people who may need them.

Another major issue for many individuals is getting prompt medical instruction and care as soon as a health problem occurs. To detect an occupying health problem in time and then to provide a prompt health care is crucial to the individual's health. For example, a heart attack victim will have a significantly greater chance of full recovery if medical care is received as soon as a heart attack is detected. As another example, an early detection of the sleep apnea can give an individual good opportunity to take necessary actions to prevent the serious sleep-disordered breathing problem from developing. Unfortunately, an individual usually does not recognize the early signs which indicate an occurring risk. Quite often, by the time the individual does realize an occurring risk, they might be incapable of seeking for medical assistance. Another issue is to provide quick and accurate information for the necessary medical care, which is essential to a successful diagnosis and treatment of the health problem.

The patent application U.S. Pat. No. 6,579,231, Personal Medical Monitoring Unit and System by Phipps, has disclosed a personal medical monitoring unit and system, which is a portable unit worn by a subject, comprising a medical monitoring device, a data processing module with memory and transmitter for collecting, monitoring, and storing the subject's physiological data and also issuing the subject's medical alarm conditions via wireless communications network to the appropriate location for expeditious dispatch of assistance. The unit also works in conjunction with a central reporting system for long term collection and storage of the subject's physiological data. The unit may have the capability to automatically dispense chemicals that may alleviate or assist in recovery from an illness. The Personal Medical Monitoring Unit and System disclosed in the invention continuously monitors a subject's medical data values as it receives them from the medical monitoring devices, which may be any standard medical monitoring device that is capable of providing data to another device. The invention has focused on the personal portable unit with data processing capability in connection with various types of medical monitoring devices through utilizing wireless communication technology.

Cox, et al. disclosed another healthcare system in the patent U.S. Pat. No. 4,679,144. In this patent, an apparatus for monitoring EKG information includes a programmable apparatus carried by an ambulatory patient for performing continuous, real-time analyses of EKG information derived from the patient. The apparatus facilitates the determination of the existence of various conditions based on these analyses which portend cardiac complications including myocardial ischemia, and arrhythemia activity and further instructs the patient on the manner of treatment required for the detected condition. As stated, the healthcare system is for ambulatory patient and only monitors EKG related information.

Oliver, et al. has presented a technical report (MSR-TR-2005-182) "HealthGear: A Real-time Wearable System for Monitoring and Analyzing Physiological Signals". HealthGear as proposed is a real-time wearable system for monitoring, visualizing and analyzing physiological signals. The data streams from the physiological sensors are constantly transmitted to a cell phone via Bluetooth for signal processing and message display. Because of wireless transmission via Bluetooth and constant data streams between sensors and cell phone, the power consumption of the system is high and the size of the monitoring system is still large. A summary up to the date is present, in which various researches on wearable health monitoring technologies and devices have been reviewed. Most of research and developments have been focused on non-invasive physiological sensors, wireless sensor network such as Personal Area Network (PAN) or Body Area Network (BAN), real-time physiological signal monitoring and cellular connection to a medical center through wireless connection via Bluetooth to a cell phone.

All available health monitoring systems and proposed inventions up today have the similar challenges for an easy wearable healthcare system with small size, low power consumption, low cost and high intelligence without limiting user's freedoms and mobility. One of the top common challenges is the communication among various sensors, central processing unit and the user. Therefore, most of the front-running research and development for the wearable healthcare system has focused on wireless sensor network such as Personal Area Network (PAN) or Body Area Network (BAN) for the sensor data transmission between sensors and central processing unit. Although wireless technology for local area network has made it possible to communicate the constant data streams of sensors to the central processing unit, it has serious limitations such as system complexity, device size, power consumption, reliability of the wireless body area network, interference from environment and user health affection possibly induced by the constant wireless signals around body all the times. Therefore, if possible, it is always desired to minimize the use of wireless for the concerns of environment interference, possible health affection caused by RF signal field, device size, power consumption and affordability for majority of population.

Accordingly, there is a need for an intelligent healthcare system and service that can provide continuous and intelligent health monitoring, analyzing and storing a subject's medical information while allowing the subject complete freedom and mobility with extremely small size, easy to wear, low power consumption, low cost, high intelligence and reliable to use with the minimized use of wireless communication for the emergent or requested communication.

SUMMARY OF THE INVENTION

The present invention is for continuous real-time monitoring subject's health condition with intelligent detection and analysis capability, smart warning or reminder of an urgent health condition and storage of an individual's health information without interrupting an individual's daily life. In the present invention, the unique advantages of specific body position around the ear have been identified and used for easy wear, easy acquiring rich physiological signals and activity signals, easy communication between various sensors and the central processing module, and easy to emit and receive smart audio outputs between the system and user without using wireless body area network. As the further advantage, the present invention can let system to load doctor's voice as warning/reminding/instruction message or the voice from a family member for reminding purpose, in which the emotional factor is considered to make the users, especially elder one, feel warm and natural to take the necessary action.

The present invention has unique advantages over any available healthcare products and proposed inventions: 1). Use the specific body position around the ear for easy wear and comfortable to wear; 2). Use the specific body position around the ear to access many critical physiological signals for easy detection and less sensitive to the environment temperature; 3). Use the specific body position around the ear for easy emitting and receiving smart audio outputs for advice, reminder or warning; 4). With these three critical advantages, it has even more attractive overall system advantage that the intelligent healthcare system may not need to use wireless local area network or body area network among sensors, the central processing unit and the user. Because of these four unique and extremely smart advantages, the said intelligent healthcare system has less technical problems and challenge usually existing for the wearable health systems. As the final benefits, the said intelligent healthcare system has much smaller size, much lower power consumption, much less complicated design, much more reliable performance, much easier to wear and much lower cost compared with the other proposed wearable health systems using wireless body area network or local area network approaches.

The present invention uses an intelligent signal processing algorithm to continuously monitor a subject's vital signs with real-time detection and analysis, record and storage of the health information running on a powerful but mini-size signal processor with low power consumption in connection with physiological sensors and activity sensors, and utilizing wireless communications technology known in the art to connect with the medical care center, doctor or family member via the available PDA or cell phone. The saved health information may then be downloaded into a computer or medical device for further analysis and evaluation. In addition, the invented monitoring device may also provide real-time health information to the monitored subject at a touch of a button as either smart audio outputs or display on available PDA or cell phone, or both of them in the same time.

Once the invented healthcare system detects a concerned health condition in the subject, which may correlate with the subject's activity detection, it can alert the subject or notify the appropriate people so that the subject can take necessary action accordingly. In addition to issue some types of alarms such as a loud beep sound to alert the subject, the device can issue the pre-recorded audio messages for specific health condition as smart warning, advice or reminder. If a serious or dangerous health condition is identified in the subject, the device may issue smart audio warning to the subject and automatically use the integrated short range RF link between the device and the PDA or cell phone to request the PDA or cell phone to make a contact with medical center, doctor or family member through the available wireless network. The device may be programmed such that a call to 911 is immediately made and the subject's name and medical history are provided therewith. At the same time, the invented device may also provide the 911 operator with the subject's location, by sending them a global positioning satellite (GPS) coordinate if GPS capability has been included in the PDA or cell phone device. It is possible to use the PDA or cell phone via the short range RF link to display the health state and dynamic health signal so that the subject or other person around can observe them.

Accordingly, it is an object of the present invention to provide an intelligent healthcare system that may be worn on a subject over the ear and carried anywhere with using non-invasive monitoring technology. The intelligent healthcare system may be setup to store current medical information and detect any pre-defined alarm conditions, such as heart attack. Upon an occurrence of such alarm conditions, the device may provide smart audio outputs such as warning, advice or reminder to the subject for a concerned situation or contact the healthcare center, doctor or family member with health information for the necessary healthcare or medical assistance for serious situation.

It is another object of the present invention to combine the advantages of the global positioning system (GPS) for locating the subject at the time of the health crisis. The communications capabilities of a cellular phone or a two way pager would provide the most prompt emergency assistance.

It is still another object of the present invention to provide a service for health information collection and long term storage of a remote subject's medical data via wireless communications technology.

It is still another object of the present innovation to provide an audio interface with media player, phone receiver through the short range RF link, or even hearing enhancement capability over the basic healthcare functionalities.

It is still another object of the present innovation to provide the other factor detections such as environment detection, weather detection, acoustic signal detection or even subject's emotion detection.

BRIEF DESCRIPTION OF THE DRAWINGS

For a better understanding of the present invention and to show more clearly how it may be carried into effect, reference will now be made, by way of example only, to the accompanying drawings which show preferred embodiments of the present invention and in which:

FIG. 1 is a system overview illustrating the present invention in a preferred embodiment.

FIG. 2 is a system application overview illustrating the present invention in the preferred embodiment.

FIG. 3 is a system diagram illustrating the present invention in the preferred embodiment.

FIG. 4 is a block diagram illustrating an example of physiological sensor unit with the intelligent signal processing capability.

FIG. 5 is a block diagram illustrating an example of activity sensor unit with the intelligent signal processing capability.

FIG. 6 is a block diagram illustrating the health monitoring principle of an intelligent healthcare system in the preferred embodiment.

DETAILED DESCRIPTION OF THE INVENTION

FIG. 1 is a system overview illustrating the present invention in a preferred embodiment. The system consists of physiological sensors (S1) and body temperature sensor seamlessly contacting the skin behind the ear, activity sensors (S2), a central processing module (CPM), a speaker for smart audio outputs, an audio delivery path with the audio interface, a contact sensor touching the skin behind the ear, a battery as system power supply, a short range RF communication unit (RF) and a shell to contain the system. The FIG. 1 also contains the adjustable user setting for system optimization, user cancel for self-confirmation to eliminate possible false alarm and user request for user to check current health state or issue a necessary urgent request. The invented system is a mini-size device designed to be worn on the ear by a subject, providing the subject with great mobility and comfort.

FIG. 2 is a system application overview illustrating the present invention as the intelligent health device and system connected to the healthcare center, doctor or family member through cellular network or any wireless network via PDA or cell phone available in the art. The urgent contact, health information or location can be transmitted as either user request or automatically generated by the intelligent healthcare system. The intelligent health system also can receive instructions or other information from the healthcare center, doctor or family member. In the meantime, the PDA and/or cell phone can be used to display the health information or save the medical data from the intelligent healthcare system when necessary or required by the user. The personal healthcare system is able to communicate with the PDA or cell phone within the short distance of arm coverage such as 1.5 m via the short range RF link. On the other side, the PDA or cell phone can connect the healthcare center, doctor or family member without distance limitation as long as commercial wireless communication coverage available.

FIG. 3 is a system diagram illustrating the present invention as an intelligent medical monitoring device and system. In the preferred embodiment, the monitoring system 1 continuously monitors a subject's physiological signals and/or activity signals as it receives them continuously from the physiological sensors and physical activity sensors. The system consists of a central processing module CPM 11, physiological sign sensors (S1) 21, activity sensors (S2) 22, a contact sensor 23, a speaker 41 for smart audio outputs, an audio path 42 with audio interface 43 to the ear canal without affecting normal acoustic signal access to the eardrum, a RF communication unit 44, an I/O interface 45, a battery 51 to power the system and a shell 52 to contain the system. The FIG. 3 also contains the user controls including user setting unit 31, user cancel 32 and user request 33. In the invented system, one or multiple vital life sign sensors 21 for detecting the subject's physiological condition such as SpO2, glucose or other signals. In its preferred embodiment of the present invention, activity sensors 22 are for detecting the subject's physical activity. The unit CPM 11 is typically comprised of a central processing unit (CPU) and memory with intelligent signal processing algorithm running in real-time.

FIG. 4 is a physiological monitoring unit, associated with physiological sensors 21 (including, for example, temperature sensor 210 and life sensors 211 . . . 21N), which can continuously monitor physiological condition such as oxyhemoglobin saturation (SpO2), body temperature or even glucose. It is extremely important to use noninvasive monitoring technology for continuous, painless and bloodless measurements for physiological signal monitoring. In the example of using physiological sensors for oxygen saturation detection, the red light (with 660 nm wavelengths) and infrared light (with 910 nm wavelengths) are emitted through the earlobe by light sources of sensor unit (S1) and to use optoelectronic sensors to detect the amount of light reflected back from the reflection plate, in which lights have gone through the earlobe twice by reflection. In addition to obtaining real-time blood oxygen level and plethysmographic signal, the intelligent detection algorithm extracts heart rate, blood flow information or even sleep apnea when the subject is in sleep. Another example of such physiological sensor is to use near-infrared light (with wavelengths between 1000 nm and 2500 nm) to detect the glucose in the similar principle. The real-time physiological detection algorithm continuously monitors the subject's physiological signals, extracts its pattern, predicts the trend of the physiological condition and analyze the physiological condition according to the medical expert knowledge and the subject's own health history. In the physiological monitoring unit, the body temperature may also be monitored since it offers basic physiological information of a subject, which can be used to help to analyze the subject's health condition.

FIG. 5 is the activity monitoring unit, associated with activity sensors 22 (which may include a plurality of activity sensors 221, 222, and 223), which can continuously monitor the subject's physical activity in XYZ dimensions for motion detection including fall detection. There are many types of activity sensors available and the example of the smallest activity sensors are piezo-resistive 3-axis acceleration sensors. The real-time activity detection algorithm continuously detects the subject's activity information such as rest, walk or run, and amount of the activity over time. The extracted activity information such as activity state, activity strength and duration can offer important correlation information for health condition evaluation in addition to be used for analyzing the subject's life style, exercise pattern and health plan. A fall detection capability may be included in the activity monitoring, which is especially valuable for the elder people since the fall for the elder people are very dangerous and need lot of attention.

FIG. 6 is a block diagram illustrating health monitoring principle of an intelligent healthcare system in the preferred embodiment, in which either the physiological information detected from the physiological monitoring unit or the activity information detected from the activity monitoring unit are analyzed, or both of them are analyzed accordingly with the correlation of these signals. The health diagnose is conducted with the use of expert knowledge and subject's health reference. The health state is determined and updated along time. If a concerned health state is detected, the system will emit smart audio outputs to alert or remind the subject for the concerned health condition. If a serious or dangerous health state is detected, the intelligent healthcare system will both emit the smart audio outputs to the subject and request, via the short range RF link, the PDA or cell phone to contact the health center, doctor or family member through the available wireless communication network. The subject has the opportunity to cancel such urgent contact if the subject feels he/she can handle the serious situation or can get the help nearby. Therefore, only if the subject feels necessary to make such an urgent contact or he/she is incapable of canceling such an urgent contact, the PDA or the cell phone will make the urgent contact and translate the necessary information.

With the integration of the physiological signal monitoring and physic activity monitoring, the present monitoring system can make more intelligent and more reliable health detection since the health condition can be highly associated with the user's physical activity condition. For example, at normal resting condition, a heart rate of 60~100 per minute for a subject can be treated as normal. A jump to 120 or higher at the same activity condition for the same subject can imply a health condition change. However, if the subject is going through a activity change from the resting condition to run condition, such a heart rate jump can be considered as normal because the intense activity usually results in a heart rate jump within a certain range. If the heart rate jumps much higher than the normal range, it is still necessary to be detected as the health problem. In the case that the heart rate becomes very low, it is another important health condition to identify. In another case, if the heart rate becomes irregular, such as missing heart beat or irregular beat duration along time, it can also imply a heart issue.

The contact sensor 23 is included to ensure that the device has been properly installed on the designed position to obtain the physiological and/or activity signals. Any improper position or installation of the device has adverse impact on the signal quality and monitoring reliability. Once an improper installation of the device is detected, the device will issue an audio warning signal such as long beep or voice warning (e.g. "Please check the device position") so that the user can make sure the device works properly.

Depending on the health condition detected by the monitoring system, various output actions can take place. Examples of output actions that may be triggered are an emergency call/transmission (page or phone call) through RF 44 for a very serious condition, activation of the smart audio outputs such as beep, advice, reminding or warning through speaker 41, audio path 42 and audio interface 43 to the ear canal for a concerned health condition, data storage on the CPM or transmission through RF 44 for the future analysis or review purpose. The medical expert knowledge is applied to the obtained information with the subject's health data, the pre-determined alarm setting and urgent contact requirement.

The monitoring system 1 includes a RF unit 44 to communicate with a PDA or cell phone, which consists of a RF transmitter for one way communication to send out the subject's health urgent condition that may include the detailed health information or subject's personal information; or a RF transceiver for dual way communication to send out health information and to receive the necessary medical or action instruction. The RF unit of the intelligent healthcare system is designed to communicate with the PDA or cell phone for the short distance coverage such as 1.5 m to save system power consumption as the subject will carry the PDA or cell phone all the time within the coverage, The monitoring system 1 may also communicate, through the RF unit 44, with a PDA or cell phone that may have included the global positioning or navigation system capability (GPS) so that the user's current geographical location can be identified by the clinic center, doctor or family member.

The user setting 31 of the invented monitoring device can be adjusted by the subject for regular monitoring over a long duration such as 30 minutes, 5 minutes or 1 minute for power saving purpose or for continuous monitoring. Even working in the different user setting modes, the system can adopt the health situation adaptively to real-time continuous mode in case of health issue detected. Therefore, the system can achieve both power saving purpose and full-on engagement monitoring when necessary.

The user cancel 32 is to cancel an automatic emergent call when an urgent and serious health condition is detected by the intelligent health system. Only if the user thinks it is necessary to send this request or the user is incapable to cancel the emergent request, the user can cancel such a request to reduce the false alarm.

The user request 33 is for the user to request a current health state update or an urgent call. The button of user request can be pushed shortly for the current medical state update as smart audio outputs or displayed over the available PDA or cell phone. The same button of user request can be pushed with hold for a certain time such as 2 seconds as an urgent call. In this case, the critical health information of the user may be sent to clinic center, doctor or family member to determine the subject's health condition and the necessary help. This user control enables the user to be able to check his/her health state or manually seek necessary assistance for a variety of conditions, including injuries from a fall or an automobile malfunction. It is also beneficial to provide the geographical coordinate locations with the emergency call if the GPS capability is included in the PDA or cell phone. Another example of user controls is to request a data-save action in conjunction with the intelligent signal processing so that the user or doctor can obtain the necessary medical information for the time being the user feels or wants to save.

The intelligent healthcare system may include a Device ID, which comprises a unique identifier for each monitoring device and its user. This identifier may be included with data transmission, and is used by the receiving end (e.g., 911 call center or clinic center) to identify the source device of each transmission. Each device ID is mapped to a particular subject, so that the receiving center can identify the subject and take the necessary action to response the request or inform the user's family member.

The intelligent healthcare system may include the basic subject profile such as name and contact phone number in the data transmission for the particular subject wearing the device. The subject profile may include more subject information such as medical history and current medical conditions. This is useful for situations in which a Subject Profile Database is not available. For example, if the device transmitter is a cell phone, and a call is triggered to a 911 call center which does not have access to the Subject Profile Database, the device may transmit the subject identifier, name, address, medical history, current medical conditions, current geographical coordinate locations (from GPS coordinates if available) and other information as necessary to the call center.

Upon the detection of the urgent health condition, the intelligent healthcare system may start a transmission sequence that includes dialing sequences for issuing a page or phone call. A device may have more than one transmission sequence. For example, one sequence may be used to call a 911 call center for an emergency condition, and the other sequence may be used to call the clinic center for status reporting. Another sequence may be used to call a family doctor or the family member for help.

Historical and current health information can be collected from the monitoring device for a specified period of time, or for a specified number of data collections. The health information is extracted and saved on the device, or it is sent out in an emergency transmission. For information only purpose, the health information such as heart rates or sleep apnea collected over certain time duration such as every 15 minutes for the past week or month may be analyzed and then updated. The information may be extracted and downloaded to a computer on a periodic basis for observation or evaluation purpose.

I/O Interface 45 is the standard communication interface such as Universal Serial Bus (USB) port between the system and the external computer or device. The health information can be downloaded to the external computer or device for further analysis; the new system code or the new parameters can be uploaded into the system to upgrade the system or performance.

Battery 51 is a low voltage power supply such as 3V or lower for the whole system. The battery may be one-time battery, rechargeable battery or any new type of power supply. The system has one or multiple internal battery level thresholds to trig the pre-set low battery warning or the system continuously checks the battery level with the pre-set thresholds. Once a low battery level is reached, the system will emit a corresponding low battery reminder or warning signal to inform the user to exchange a new battery or recharge the battery. In the meantime, the system will make the necessary update or save the most recent health information.

The monitoring device is usually worn by a user on the specified position around the ear. That is, people with health concern or health history can use the present monitoring device for health assistant device, or people with no known medical history can use the present monitoring device as a safeguard or simply a self-health check/survey purpose; athletes may employ the present devices to monitor their own physical condition during competition, practice or training; parents may use the present invention to monitor and care for their children or infants, and the most importantly, the elder people can use the present device to monitor their physical activity and health condition during their daily life.

The intelligent healthcare system of the present invention can be many types of medical monitoring device. With the medical progress, many new medical sensors with new detecting technology can be integrated into the present invented system. Examples of detection include: blood oxygen level, heart rate or pulse, blood flow information, body temperature, sleep apnea, glucose, exercise amount, unexpected fall or any type of health sign or activity that may be detected by the monitoring device.

The aspects of the present invention can be scaled down for physiological signal monitoring system only or activity monitoring system only without departing from the spirit or essential attributes thereof. On the other side, the aspects of the present invention can be expanded to include more signal detections such as environment detection, weather detection, acoustic signal detection or even subject's emotion detection, in addition to the described health monitoring, without departing from the spirit or essential attributes thereof.

The invention claimed is:

1. A healthcare system comprising:
a shell configured to be worn behind an ear of a subject;
a plurality of physiological sensors proximate to the shell for measuring and outputting physiological variables representing a physiological condition of the subject wherein the physiological sensors are positioned at the ear of the subject and wherein the physiological sensors comprise an oximetry sensor (SpO2), temperature sensor, or glucose sensor;
a three dimensional activity sensor housed in the shell for measuring and outputting an activity variable representing activity of the subject;
at least one environmental sensor proximate to the shell that measures and outputs an environmental temperature;
a processor housed in the shell for processing and analyzing the environmental temperature and the physiological and activity variables and for generating an output signal based on the analysis of the environmental temperature and the physiological and activity variables and wherein the processor processes the environmental temperature, physiological and activity variables to determine a health variable representing the subject's health condition and the output signal is based on the health condition and wherein the processor further correlates data from the activity sensor and the health variable to detect a fall, and wherein the processor is configured to process the physiological and activity variables to determine a respiratory rate and the output signal is based on the respiratory rate calculated based on blood flow; and
an output device proximate to the shell for receiving the output signal and for outputting said output signal to notify the subject of the health condition.

2. The healthcare system as in claim 1, wherein the output device is a speaker and the output signal is an audible signal and wherein the healthcare system further comprises an audio path, a physical member adapted to transmit the audible signal from the speaker to an audio interface located adjacent to the subject's ear.

3. The healthcare system of claim 2, wherein the audible signal comprises a voice message to the subject.

4. The healthcare system of claim 3, wherein the voice message to the subject comprises a recorded message from a family member of the subject.

5. The healthcare system of claim 1, further comprising an adaptive module for providing feedback to the processor to adjust the output signal based on the feedback.

6. The healthcare system of claim 1, further comprising a contact sensor to determine if the shell of the healthcare system is properly positioned.

7. The healthcare system of claim 6, wherein the processor provides an alarm if the contact sensor determines that the shell is not properly positioned.

8. The healthcare system of claim 1, further comprising a communications interface for downloading and uploading data.

9. The healthcare system of claim 8, wherein said data comprises device identification and a subject profile including subject's name, home address, medical history and current measurements.

10. A healthcare system comprising:
a shell configured to be worn behind an ear of a subject;
a plurality of physiological sensors proximate to the shell for measuring and outputting a physiological variable representing a physiological condition of the subject wherein the physiological sensors are positioned at the ear of the subject and wherein the physiological sensors comprise at least one of an oximetry sensor (SpO2), temperature sensor, or glucose sensor;
a three dimensional activity sensor housed in the shell for measuring and outputting an activity variable representing activity of the subject;
a processor housed in the shell for processing and analyzing the physiological and activity variables and for generating an output signal based on the analysis of the physiological and activity variables and wherein the processor processes the physiological and activity variables to determine a health variable representing the subject's health condition and the output signal is based on the health condition and wherein the processor further correlates data from the activity sensor and the health variable to detect a fall, and wherein the processor is configured to process the physiological and activity variables to determine a respiratory rate and the output signal is based on the respiratory rate calculated based on blood flow; and an audio path, an physical member adapted to transmit the audible output signal from a speaker housed in the shell and outputting the audible output signal to an audio interface located adjacent to the subject's ear, such that the audio path does not affect normal acoustic signal access to the eardrum.

11. The healthcare system of claim 10, further comprising an environmental sensor wherein the environmental sensor measures and outputs an environmental temperature.

12. The healthcare system of claim 10, wherein the audible signal comprises a voice message to the subject.

13. The healthcare system of claim 12, wherein the voice message to the subject comprises a recorded message from a family member of the subject.

14. The healthcare system of claim 10, further comprising an adaptive module for providing feedback to the processor to adjust the output signal based on the feedback.

15. The healthcare system of claim 10, further comprising a contact sensor to determine if the shell of the healthcare system is properly positioned.

16. The healthcare system of claim 15, wherein the processor provides an alarm if the contact sensor determines that the shell is not properly positioned.

17. The healthcare system of claim 10, further comprising a communications interface for downloading and uploading data.

18. The healthcare system of claim 17, wherein said data comprises device identification and a subject profile including subject's name, home address, medical history and current measurements.

* * * * *